United States Patent

Horn et al.

[11] Patent Number: 6,024,752
[45] Date of Patent: Feb. 15, 2000

[54] SOFT FLEXIBLE TIPPED BALLOON

[75] Inventors: Daniel J. Horn, Shoreview; Victor L. Schoenle, Greenfield, both of Minn.

[73] Assignee: Scimed Life Systems, Inc., Maple Grove, Minn.

[21] Appl. No.: 09/076,252

[22] Filed: May 11, 1998

[51] Int. Cl.[7] .................................................. A61M 29/00
[52] U.S. Cl. ............................................. 606/192; 606/194
[58] Field of Search .................................. 606/192, 194, 606/195, 159

[56] References Cited

U.S. PATENT DOCUMENTS

| Re. 32,983 | 7/1989 | Levy | 428/36.92 |
|---|---|---|---|
| Re. 33,561 | 3/1991 | Levy | 428/36.92 |
| 4,413,989 | 11/1983 | Schjeldahl et al. | 604/96 |
| 4,456,000 | 6/1984 | Schjeldahl et al. | 128/1 D |
| 4,490,421 | 12/1984 | Levy | 428/35 |
| 4,906,244 | 3/1990 | Pinchuk et al. | 606/194 |
| 4,963,313 | 10/1990 | Noddin et al. | 264/573 |
| 5,087,394 | 2/1992 | Keith | 204/22 |
| 5,108,415 | 4/1992 | Pinchuk et al. | 606/194 |
| 5,156,612 | 10/1992 | Pinchuk et al. | 606/194 |
| 5,270,086 | 12/1993 | Hamlin | 428/36 |
| 5,304,340 | 4/1994 | Downey | 264/521 |
| 5,334,146 | 8/1994 | Ozasa | 604/96 |
| 5,358,486 | 10/1994 | Saab | 604/96 |
| 5,415,635 | 5/1995 | Bagaoisan et al. | 604/96 |
| 5,443,495 | 8/1995 | Buscemi et al. | 623/1 |
| 5,447,497 | 9/1995 | Sogard et al. | 604/101 |
| 5,470,313 | 11/1995 | Crocker et al. | 604/96 |
| 5,512,051 | 4/1996 | Wang et al. | 604/96 |
| 5,514,092 | 5/1996 | Forman et al. | 606/194 |
| 5,556,383 | 9/1996 | Wang et al. | 604/96 |
| 5,733,301 | 3/1998 | Forman | 606/192 |

FOREIGN PATENT DOCUMENTS

| 457 456 A1 | 5/1990 | European Pat. Off. . |
|---|---|---|
| 485903 A2 | 5/1992 | European Pat. Off. . |
| 318 919 B1 | 1/1994 | European Pat. Off. . |
| 95/09667 | 4/1995 | WIPO . |
| 95/22367 | 8/1995 | WIPO . |
| 96/04951 | 2/1996 | WIPO . |

*Primary Examiner*—Michael Buiz
*Assistant Examiner*—Vy Q. Bui
*Attorney, Agent, or Firm*—Vidas, Arrett & Steinkraus

[57] ABSTRACT

A soft flexible tipped balloon for a medical device, the balloon comprising a first balloon segment made of a first polymer material, a second balloon segment made of a second polymer material, the second polymer material different from the first polymer material, and a third balloon segment made of a third polymer material, the third polymer material different from the second polymer material and optionally different from the first polymer material, the segments arranged sequentially along the length of the balloon and processes of making the same.

32 Claims, 2 Drawing Sheets

SOFT FLEXIBLE TIPPED BALLOON

BACKGROUND OF THE INVENTION

Balloons mounted on the distal ends of catheters are widely used in medical treatment. The balloon may be used to widen a vessel into which the catheter is inserted or to force open a blocked vessel. The requirements for strength and size of the balloons vary widely depending on the balloon's intended use and the vessel size into which the catheter is inserted. Perhaps the most demanding applications for such balloons are in balloon angioplasty in which catheters are inserted for long distances into extremely small vessels and used to open stenoses of blood vessels by balloon inflation.

Applications such as balloon angioplasty require extremely thin walled high strength relatively inelastic balloons of predictable inflation properties. Thin walls are necessary because the balloon's wall and waist thicknesses limit the minimum diameter of the distal end of the catheter and therefore determine the limits on vessel size treatable by the method and the ease of passage of the catheter through the vascular system. High strength is necessary because the balloon is used to push open a stenosis and so the thin wall must not burst under the high internal pressures necessary to accomplish this task. The balloon must have some elasticity so that the inflated diameter can be controlled, so as to allow the surgeon to vary the balloon's diameter as required to treat individual lesions, but that elasticity must be relatively low so that the diameter is easily controllable. Small variations in pressure must not cause wide variation in diameter.

At the same time, the balloon must also possess excellent crossing, recrossing and tracking properties. It is highly desirable for the balloon to be expandable more than once to a reproducible expanded position from an initial folded position. It is also desirable that on deflation the deflated balloon return to its initial configuration. Finally, it is desirable for the balloon to be easily maneuvered through the body lumen. These properties are determined in large measure by the cone section of the balloon. Because the hoop stress is lower in the cone than in the body of the balloon, material comprising the cone section need not be as strong as the material in the body section. Thus, materials which are softer and more flexible may be used to form the cone section, thus allowing for greater crossing and recrossing properties while facilitating tracking.

There are a number of different approaches in the prior art to designing a balloon having differing physical and mechanical properties in different sections of the balloon.

One such approach involves forming a balloon by stretching and blowing of the balloon from a segment of extruded polymer tubing. Balloons produced by stretching and blowing a tubular preform or "parison" typically have much thicker waist and cone walls than the wall thickness of their body portions. The thicker cone walls contribute to the overall thickness of the catheter, making tracking, crossing and recrossing of lesions more difficult. Further, thick cones interfere with refolding of the balloon on deflation so that the deflated balloon can only be further inserted or withdrawn with difficulty, occasionally even damaging the blood vessel.

While there have been several solutions proposed for reducing the cone or waist thickness of catheter balloons in U.S. Pat. No. 4,906,241, U.S. Pat. No. 4,963,313, U.S. Pat. No. 5,304,340, U.S. Pat. No. 5,087,394, EP 318,919, EP 485,903, the procedures involved in these references are quite cumbersome.

Another approach involves the formation of layered balloons, wherein more than one layer of material is employed in certain regions of the balloon. The layers may be of a same or different material.

To that end, U.S. Pat. No. 5,358,486 to Saab discloses a multiple layer balloon. The balloon is built from a plurality of layers of material. The inner layer defines a complete layer. Each subsequent outer layer is trimmed to be shorter than the next adjacent innermost layer. The trimming is effected in the cone regions.

WO 95/09667 discloses a dilatation balloon formed of layers of a noncompliant structural polymer inner layer and a soft, abrasion resistant, elastomeric outer layer.

Unfortunately, the use of layering to achieve certain physical and/or mechanical properties can result in a thicker balloon than is desired.

It is a goal of the present invention to provide a balloon for a catheter device that is characterized by high strength and excellent crossing and recrossing properties while having a soft tip for ease of tracking, without the drawbacks of the prior art devices.

For the sake of clarity, the term 'segment' shall refer to the individual pieces of material that are joined together to form the balloon. As such, the term 'segment' is intended to include tubing and more generally, preforms. The term 'section' shall refer herein to a region of a balloon or balloon preform (such as, for example, a cone section, a body section or a waist section).

SUMMARY OF THE INVENTION

The present invention is directed in general to a balloon for a medical device, the balloon comprising a plurality of balloon segments. At least two of the segments are made of different polymer materials. The segments are arranged sequentially along the length of the balloon.

In one aspect, the present invention is directed to a balloon formed of two such segments.

In another aspect, the invention is directed to a balloon comprising three segments arranged longitudinally. The balloon comprises a first balloon segment made of a first polymer material, a second balloon segment made of a second polymer material, the second polymer material different from the first polymer material, and a third balloon segment made of a third polymer material, the third polymer material different from the second polymer material but optionally the same as or different from, the first polymer material. The first, second and third segments are arranged sequentially along the length of the balloon.

The invention also pertains to processes of preparing such balloons. One such process utilizes a balloon preform prepared by joining three segments of tubing end-to-end via the use of heat or adhesives. The process comprises the steps of providing a first finished balloon segment made from a first polymer material, a second finished balloon segment made from a second polymer material, the second balloon segment having a lip cut in each of the two ends of the balloon segment and a third balloon tubing segment comprising a third polymer material, joining one end of the first balloon segment with the first lip on the second balloon segment, and joining the second lip on the second balloon segment with the first end of the third balloon segment.

The invention further pertains to a process of preparing such balloons by sequentially extruding the segments of the balloon. The process comprises the steps of sequentially extruding first, and second polymer materials, as well as any other additional polymer materials and then subjecting the preform to a conventional blowing. In the case of three polymer materials, the first polymer material forms a first segment of the balloon, the second polymer material forms a second segment of the balloon and the third polymer material forms a third segment of the balloon.

The present invention is also directed to the balloon manufactured according to the above process of extrusion.

DETAILED DESCRIPTION OF THE INVENTION

Figure 1A:
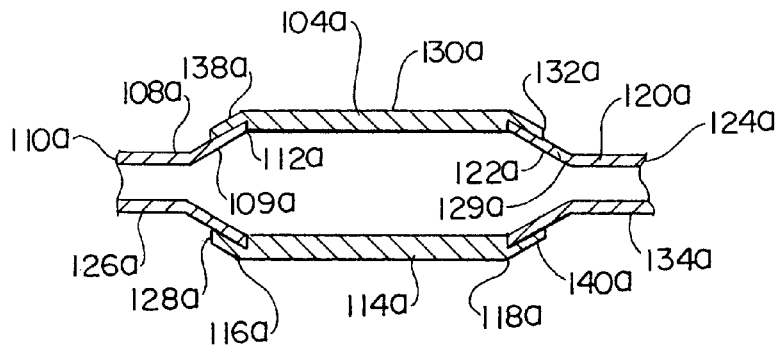
FIG. 1a shows a side plan view of a three segment balloon of the present invention.

While this invention may be embodied in many different forms, there are described in detail herein specific preferred embodiments of the invention. This description is an exemplification of the principles of the invention and is not intended to limit the invention to the particular embodiments illustrated.

The dilatation balloon fabricated by the present inventive process as illustrated generally at 104a in FIG. 1, comprises three segments arranged sequentially along the longitudinal axis of the balloon. The first segment 108a, comprising a first end 110a and a second end 112a is made of a first polymer material, the second segment 114a, comprising a first end 116a and a second end 118a, the second segment adjacent to the first segment 108a, is made of a second polymer material, the second material different from the first polymer material, and the third segment 120a, comprising a first end 122a and a second end 124a, the third segment adjacent to the second segment 114a, is made of a third polymer material, the third polymer material different from the second polymer material and optionally different from the first polymer material.

Typically, the inventive balloons, as shown in FIG. 1a, will comprise a first waist section 126a, a first cone section 128a, a body section 130a, a second cone section 132a and a second waist section 134a wherein the first balloon segment 108a comprises the first waist section 126a and a portion of the first cone section 128a, the second balloon segment 114a comprises a portion of the first cone section 128a, the body section 130a and a portion of the second cone section 132a and the third balloon segment 120a comprises a portion of the second cone section 132a and the second waist section 134a.

Figure 2:
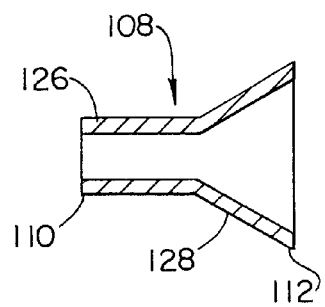
FIG. 2 shows a side plan view of a portion of the first balloon segment of the inventive balloon.
Figure 3:
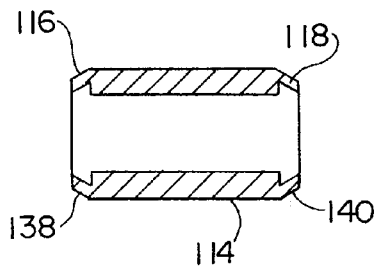
FIG. 3 shows a side plan view of a portion of the second balloon segment of the balloon of the invention.
Figure 4:
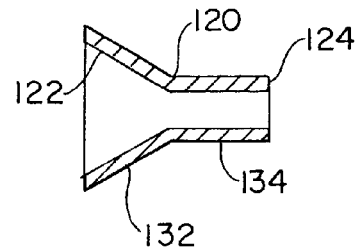
FIG. 4 shows a side plan view of a portion of the third balloon segment of the inventive balloon.

In one embodiment, the balloon of the present invention, as illustrated in FIG. 1a, comprises a first segment 108a, a second segment 114a having a first lip 138a and a second lip 140a, and a third segment 120a. The individual segments are also depicted in FIGS. 2–4. Note that the segments are depicted in FIGS. 2–4 as being shaped. This shaping may occur prior to or following the joining together of the balloon segments.

Figure 1B:
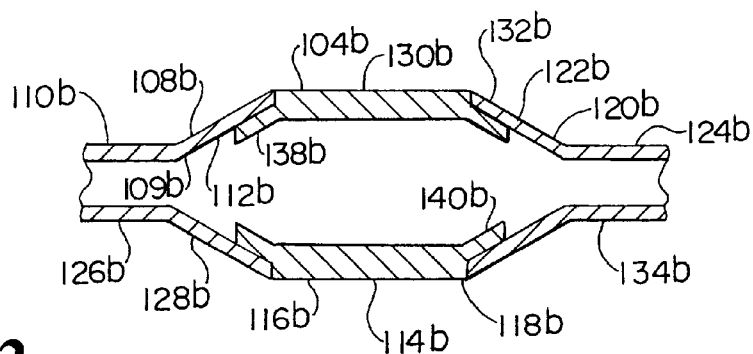
FIG. 1b shows a side plan view of another embodiment of a three segment balloon of the present invention.

In another embodiment, the balloon of the present invention, as illustrated in FIG. 1b, comprises a first segment 108b, a second segment 114b having a first lip 138b and a second lip 140b, and a third segment 120b. The embodiment of FIG. 1b differs from that of FIG. 1a in that the lips in the embodiment of FIG. 1a are cut from the inside of the middle segment outward while the lips in the embodiment of FIG. 1b are cut from the outside of the middle segment inward. In the latter case, the outer diameter of the middle segment is reduced in the region of the lips relative to the rest of the segment.

It is preferable that the junction between the first and second segments and similarly between the second and third segments occur as close as possible to the body section 130a (130b) without actually occurring in the body section.

Although the lips have been shown in FIGS. 1a and 1b as having been cut into the middle segment, they alternatively may be cut into the first and/or third segments, either from the outside inward or from the inside outward.

Figure 5A:
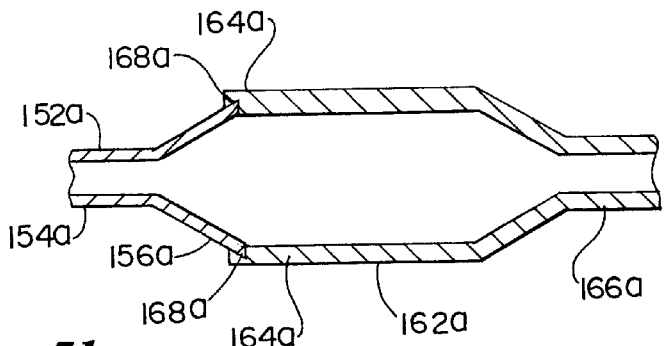
FIG. 5a shows a side plan view of a two segment balloon of the present invention.

In another embodiment, as shown in FIG. 5a, the inventive balloon is formed of a first segment 152a having first 154a and second 156a ends and formed of a first polymer material and a second segment 162a having first 164a and second 166a ends and formed of a second polymer material differing from the first polymer material. First end 164a of second segment 162a has a lip 168a cut therein so as to accommodate second end 156a of first segment 152a. First segment 152a and second segment 162a are suitably joined together.

Figure 5B:
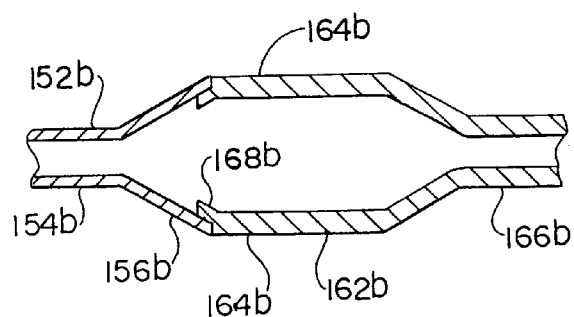
FIG. 5b shows a side plan view of another embodiment of a two segment balloon of the present invention.

In another embodiment, as shown in FIG. 5b, the inventive balloon is formed of a first segment 152b having first 154b and second 156b ends and formed of a first polymer material and a second segment 162b having first 164b and second 166b ends and formed of a second polymer material differing from the first polymer material. First end 164b of second segment 162b has a lip 168b cut therein so as to accommodate second end 156b of first segment 152b. First segment 152b and second segment 162b are suitably joined together. The embodiment of FIG. 5b differs from that of FIG. 5a in that the lips in the embodiment of FIG. 5a are cut from the inside of the second segment outward while the lips in the embodiment of FIG. 5b are cut from the outside of the second segment inward. In the latter case, the outer diameter of the second segment is reduced in the region of the lips relative to the rest of the segment.

Although the lips have been shown in FIGS. 5a and 5b as having been cut into the second segment, they alternatively may be cut into the first segments, either from the outside inward or from the inside outward.

While the embodiments shown in FIGS. 1a,b and 5a,b are formed of three and two segments respectively, the invention contemplates the formation of inventive balloons comprised of any number of sequential segments.

Although the presence of the lip is useful for bonding the segments together, it is not necessary.

The balloon segments may be joined together by heating. An internal support mandrel is inserted into the section of segment to be joined, either the second end of the first segment or the first end of the third segment, and the section of the segment to be joined thereto compressed onto the other segment with a body clamp. The joint is heated, optionally by application of radio frequency (rf) energy supplied from a rf coil in the mandrel until the segments are bonded.

Alternatively, the segments may be joined together by the use of an appropriate bio-compatible adhesive such as polyurethane or a methacrylate.

The individual segments may be stretched prior to being joined together. Alternatively, unstretched segments may be used as well. The balloon tubing may also be stretched after joining the segments together. This may prove advantageous in that the balloon tubing may preferentially stretch in the soft areas of the balloon, such as the waste and cone sections relative to the hard areas (i.e. the body section).

If the formed balloon is stretched, the balloon can optionally be pressurized during the stretching in order to maintain the inner diameter of the balloon constant.

Shaping of the balloon may be accomplished in a final blowing step after the segments have been joined.

It is possible to make the balloons from a variety of materials that are generally of the thermoplastic polymeric type. Such materials may include: polyethylenes, ionomers, ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; copolyesters; thermoplastic rubbers; silicone-polycarbonate copolymers; polyamides; and ethylene-vinyl acetate copolymers. Orientable polyesters, especially polyethylene terephthalate (PET), are among the preferred materials for forming catheter balloons. References illustrating the materials and methods of making catheter balloons include: U.S. Pat. No. 4,413,989 and U.S. Pat. No. 4,456,000 to Schjeldahl et al, U.S. Pat. No. 4,490, 421, U.S. Pat. No. Re 32,983 and Re 33,561 to Levy, and U.S. Pat. No. 4,906,244, U.S. Pat. No. 5,108,415 and U.S. Pat. No. 5,156,612 to Pinchuck et al. Where LEAP™ materials (that is, PEBAX®) are used, the segments need not be stretched prior to being joined together.

One preferred combination of materials for the balloons of the present invention is PET for the body section and a PET/Polyetherester block copolymer blend such as PET/Hytrel™ or PET/Arnitel™ for the core and waists of the balloon. Another preferred combination involves the use of different durometer PEBAX® polymers for the three sections. Balloons made of these materials are disclosed in U.S. Pat. No. 5,556,383 to Wang et al., incorporated in its entirety herein by reference. Specific grades of Arnitel™ that are suitable for use in the inventive balloons include Arnitel™ EM 740 and Arnitel™ EM 630. Hytrel™ 7246 is also suitable for use in the present invention. Another preferred combination involves the use of urethanes of varying durometer in the three sections. More generally, the invention involves the use of a polyester homopolymer or copolymer for the body region of the balloon and a softer polyester elastomer for the waist.

In one embodiment of the balloon the second polymer material is characterized by a shore D hardness greater than the shore D hardness of the third polymer material and the third polymer material is characterized by a shore D hardness greater than or equal to the shore D hardness of the first polymer material.

In another embodiment, the present invention is directed to the inventive balloons of the present application mounted on a catheter.

In the above embodiments, the presence of a lip on any given segment is advantageous for bonding purposes although not absolutely necessary. The present invention further contemplates other arrangement of lips on the various segments of the balloon. Specifically, with reference to the balloons of FIGS. 1a, 1b, rather than having lips cut in both ends of middle segment 130, lips may equally well be cut into interior sides 109 and 129 of first segment 108 and third segment 120 at second end 112 of first segment 108 and first end 122 of third segment 120, respectively. Of course, other suitable combinations of lips are contemplated as well.

The invention also pertains to processes of preparing the inventive balloons of the present application. The process comprises the steps of providing a first finished balloon segment made from a first polymer material, a second finished balloon segment made from a second polymer material, the second balloon segment having a lip cut in each of the two ends of the balloon segment and a third finished balloon segment comprising a third polymer material, joining one end of the first balloon segment with the first lip on the second balloon segment, and joining the second lip on the second balloon segment with the first end of the third balloon segment.

Another process of preparing the inventive balloons comprises providing a first segment of tubing made from a first polymer material, a second segment of tubing made from a second polymer material, the second tubing segment having a lip cut in each of the two ends of the tubing segment and a third tubing segment comprising a third polymer material, joining one end of the first tubing segment with the first lip on the second tubing segment, and joining the second lip on the second tubing segment with the first end of the third tubing segment. The resulting balloon preform may then be blown and shaped using any of the methods known in the art.

The invention further pertains to a process of preparing the inventive balloons of the present application comprising the steps of extruding tubing having sequential longitudinal segments made from respective first, second and third polymer materials, the first polymer material different from the second polymer material and the third polymer material different from the second polymer material and optionally the same as the first polymer material so as to form a balloon comprising a first segment made from a first polymer material, a second segment made from a second polymer material different from the first polymer material and a third segment made from a third polymer material different from the second polymer material and optionally the same as the first polymer material. The so formed balloon is then, optionally, subject to a stretching and/or blowing and shaping step, as is known in the art.

Figure 6:
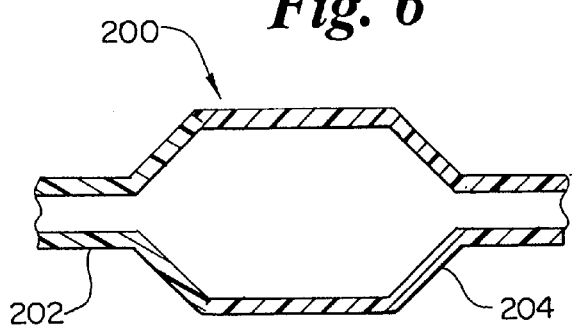
FIG. 6 shows a side plan view of an inventive extruded two segment balloon.
Figure 7:
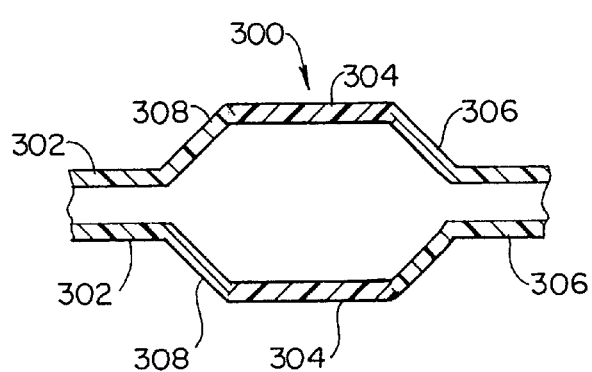
FIG. 7 shows a side plan view of an inventive extruded three segment balloon.

The invention is further directed to balloons made by the above extrusion process as shown in FIGS. 6 and 7. As shown in FIG. 6, a balloon shown generally at 200, is formed in accordance with the above extrusion process. Balloon 200 consists of a first region 202 formed of a first extruded polymeric material and a second region 204 formed of a second polymeric material. Similarly, as shown in FIG. 7, balloon 300 consists of a first region 302 formed of a first extruded polymeric material, a second region 304 formed of a second polymeric material and a third region 306 formed of a third polymeric material. The balloon prepared by extrusion may optionally have a first transition region between the first segment and the second segment and a second transition region between the second segment and the third segment. In the first transition region, the balloon will comprise a mixture of the first and second polymer materials while in the second transition region the balloon will comprise a mixture the second and third polymer materials. This is depicted in FIG. 7 where there is a transition region 308 between first region 302 and second region 304. It is desirable, however, to minimize the length of the transition regions.

The balloon formed by the inventive extrusion process may comprise a first waist section, a first cone section, a body section, a second cone section and a second waist section wherein the first balloon segment comprises the first waist section and a portion of the first cone section, the second balloon segment comprises a portion of the first cone section, the body section and a portion of the second cone section and the third balloon segment comprises a portion of the second cone section and the second waist section.

EXAMPLE 1

A 3.5 mm PET balloon tube (inner diameter 0.017 inches, outer diameter 0.043 inches) of shore D hardness in excess of 75 is heated to 90° C. and stretched 1.4 times in the direction of its axis. A lip is cut or ground into the ends of this segment to an outside diameter of 0.022 to 0.023 inches extending 1 to 2 mm back from the end. The lip is cut from the outside of the tube inward. A second segment of tubing made from a 75%/25% by weight blend of PET and Polyetherester (Hytrel® 7246) of shore D hardness between 60 and 75 is extruded to an inside diameter of 0.0235 inches and an outside diameter of 0.0295 inches. The segments are joined together via the use of heat. To effect this, a Teflon coated mandrel is placed inside the first segment and extends in to the second segment which is placed over the lip of the first segment. Pressure is applied over the junction between the segments via a collapsible collet. RF energy is directed to the junction and melts the segments together. Finally, the assembly is placed into a heated mold and is inflated by pressurized gas so as to be pressed tightly against the inside surface of the metal mold and then cooled.

Optionally, a lip may be ground into the opposite end of the PET balloon tube and a third segment of tubing may be extruded to the same dimensions as the second segment. The third segment may be joined to the opposite end of the PET tube in a method similar to that employed to joined the first two segments.

EXAMPLE 2

A 3.5 mm Pebax™ balloon tube (inner diameter 0.0234 inches, outer diameter 0.0410 inches) of shore D hardness 72 is locally heated to 93° C. and stretched in the direction of its axis to form a necked region. The necked region is equivalent to above-described lip. The outer diameter of the tube in the necked region is smaller than the outer diameter of the rest of the tube. The tube is inflated with pressurized air to support the inner diameter from collapsing. A second segment of Pebax™ tubing of shore D hardness between 63 and 70 is extruded to an inside diameter of 0.0275 inches and an outside diameter of 0.0335 inches. The segments are joined together via the use of heat. To effect this, a Teflon coated mandrel is placed inside the first segment and extends in to the second segment which is placed over the necked region (lip) of the first segment. Pressure is applied over the junction between the segments via a collapsible collet. RF energy is directed to the junction and melts the segments together. Finally, the assembly is placed into a heated mold and is inflated by pressurized gas so as to be pressed tightly against the inside surface of the metal mold and then cooled.

Optionally, a second lip may also be formed in the opposite end of the PET balloon tube by locally heating and stretching the tube. A third segment may be joined to the opposite end of the PET tube in a method similar to that employed to joined the first two segments.

EXAMPLE 3

A single tube comprising three segments may be continuously extruded. The first segment, a 3.5 mm section of tubing of inner diameter 0.017 inch, and outer diameter 0.043 inch formed of Hytrel™ 7246 may be extruded. As the extrusion of the first segment is nearly completed, PET resin may exit the extruder. The extrusion of the second segment commences with the extrusion of the PET material. A 6 mm section of PET tubing of inner diameter 0.017 inch, and outer diameter 0.043 inch may be extruded. As the extrusion of the second segment nears completion, Hytrel™ resin may exit the extruder. The extrusion of the third section commences with the extrusion of the Hytrel™. The third segment is a 3.5 mm section of tubing of inner diameter 0.017 inch and outer diameter 0.043 inch formed of Hytrel™. The extruded tube may be stretched three times in the direction of its axis forming a necked portion and thin waists in the first and third segments. The tube may be inflated by pressurized air so as to be pressed tightly against the inside surface of the metal mold and cooled.

EXAMPLE 4

A 0.010 inch thick lip may be cut into a first segment of tubing, a 3.5 mm Arnitel EM 550 balloon tube (inner diameter 0.017 inch, outer diameter 0.043 inch) of shore D hardness of less than 60. The lip is ground from the outside in, thereby reducing the outer diameter of the tubing in the region of the lip. The second segment of tubing made of Arnitel EM-740 has a shore D hardness of between 60 and 75 (inner diameter 0.0235 inch, outer diameter 0.043 inch). A third 3.5 mm segment of Arnitel EM 550 tube, of shore D hardness less than 60 may be prepared similarly to the first segment. A drop of a methacrylate based adhesive may be applied to each lip and the first and third segments bonded to respective ends of the middle segment. The ensuing tube may be put in a metal mold, heated at 85° C. and stretched three times in the direction of its axis through a restricted hot die or body clamp forming a necked portion and thin waist segment in the first and third segments. The tube may then be inflated by pressurized air so as to be pressed tightly against the inside surface of the metal mold and cooled.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A balloon for a medical device, the balloon comprising a plurality of balloon segments, at least two of the segments made of different polymer materials, the plurality of segments arranged sequentially along the length of the balloon, the balloon having a distal portion, a body portion and a proximal portion, the distal portion softer than the body portion of the balloon as measured by the Shore D hardness scale.

2. The balloon of claim 1 wherein the distal portion is softer than the proximal portion of the balloon as measured by the Shore D hardness scale.

3. The balloon of claim 1 mounted on a catheter.

4. The balloon of claim 1 wherein one of the polymer materials is characterized by a Shore D hardness of less than about 60.

5. The balloon of claim 4 further comprising a polymer material characterized by a Shore D hardness of about 60 to about 75.

6. The balloon of claim 1 wherein at least one segment includes a lip which is joined to an adjacent segment.

7. A balloon for a medical device, the balloon formed of a proximal segment and a distal segment, each segment made of a different polymer material, the distal segment made of a softer material than the proximal segment, the segments arranged sequentially along the length of the balloon.

8. A catheter with the balloon of claim 7 mounted thereon.

9. The balloon of claim 7 wherein at least one segment includes a lip which is joined to an adjacent segment.

10. A balloon for a medical device formed of three segments, a first balloon segment made of a first polymer material, a second balloon segment made of a second polymer material, the second polymer material different from the first polymer material, and a third balloon segment made of a third polymer material, the third polymer material different from the second polymer material and different from the first polymer material, the segments arranged sequentially along the length of the balloon.

11. A catheter with the balloon of claim 10 mounted thereon.

12. The balloon of claim 10 wherein the second balloon segment has a first end with a first lip cut therein and a second end with a second lip cut therein, a portion of the first balloon segment joined to the first lip of the second balloon segment and a portion of the third balloon segment joined to the second lip of the second balloon segment.

13. A balloon for a medical device, the balloon comprising
 a first balloon section made of a first polymer material,
 a second balloon section made of a second polymer material, the second polymer material different from the first polymer material, and
 a third balloon section made of a third polymer material, the third polymer material different from the second polymer material and optionally different from the first polymer material, the sections arranged sequentially along the length of the balloon,
 the balloon further comprising
  a first waist section,
  a first cone section,
  a body section,
  a second cone section and
  a second waist section
   wherein the first balloon section comprises the first waist section and a portion of the first cone section, the second balloon section comprises a portion of the first cone section, the body section and a portion of the second cone section and the third balloon section comprises a portion of the second cone section and the second waist section.

14. The balloon of claim 13 wherein the second balloon segment has a first end with a first lip cut therein and a second end with a second lip cut therein, a portion of the first balloon segment joined to the first lip of the second balloon segment and a portion of the third balloon segment joined to the second lip of the second balloon segment.

15. The balloon of claim 14 wherein the balloon segments are joined by heating the adjacent segments and pressing the segments together.

16. The balloon of claim 13 wherein the first and third polymer materials are the same.

17. The balloon of claim 13 wherein the second polymer material is characterized by a shore D hardness greater than the shore D hardness of the third polymer material and the third polymer material is characterized by a shore D hardness greater than or equal to the shore D hardness of the first polymer material.

18. The balloon of claim 13 where in the first, second and third polymer materials are thermoplastic.

19. The balloon of claim 13 wherein the second polymer material is a polyester homopolymer or copolymer and the first and third polymer materials are polyester elastomers.

20. The balloon of claim 13 formed by sequentially extruding the first, second and third balloon segments.

21. The balloon of claim 13 wherein the balloon is shaped after joining the segments together.

22. The balloon of claim 13 wherein the segments are shaped prior to being joined together.

23. The balloon of claim 13 wherein the first polymer material and the third polymer material are identical.

24. A catheter with the balloon of claim 13 mounted thereon.

25. A balloon for a medical device, the balloon comprising
 a first balloon section made of a first polymer material,
 a second balloon section made of a second polymer material, the second polymer material different from the first polymer material, and
 a third balloon section made of a third polymer material, the third polymer material different from the second polymer material and optionally different from the first polymer material, the sections arranged sequentially along the length of the balloon,
 the balloon further comprising first and second transition regions,
 the first transition region located between the first and second segments and comprising a mixture of the first and second polymer materials,
 the second transition region located between the second and third segments and comprising a mixture of the second and third polymer materials.

26. A catheter with the balloon of claim 25 mounted thereon.

27. A balloon for a medical device, the balloon comprising a plurality of balloon segments, at least two of the segments made of different polymer materials, the plurality of segments arranged sequentially along the length of the balloon, at least one segment including a lip which is joined to an adjacent segment.

28. The balloon of claim 27 consisting of two segments.

29. The balloon of claim 27 consisting of three segments.

30. The balloon of claim 27 further comprising
 a first waist section,
 a first cone section,
 a body section,
 a second cone section and
 a second waist section
  wherein the first balloon section comprises the first waist section and a portion of the first cone section, the second balloon section comprises a portion of the first cone section, the body section and a portion of the second cone section and the third balloon section comprises a portion of the second cone section and the second waist section.

31. The balloon of claim 27 having a distal and a proximal end, the distal end made of a softer polymer material than the proximal end.

32. A balloon for a medical device, the balloon consisting of two segments, each segment made of a different polymer material, the segments arranged sequentially along the length of the balloon.

* * * * *

UNITED STATES PATENT AND TRADEMARK OFFICE
CERTIFICATE OF CORRECTION

PATENT NO. : 6,024,752

DATED : February 15, 2000

INVENTOR(S) : Horn et al

It is certified that error appears in the above-identified patent and that said Letters Patent is hereby corrected as shown below:

On the Title Page, Item [56] References Cited, the following should be added:

| | | | |
|---|---|---|---|
| 5,587,125 | 12/1996 | Roychowdhury | 264/515 |
| 0 669 143 A1 | 08/1995 | European Pat. Off. | |
| 97/17889 | 5/1997 | WIPO | |

Signed and Sealed this

Twenty-seventh Day of March, 2001

Attest:

NICHOLAS P. GODICI

Attesting Officer

Acting Director of the United States Patent and Trademark Office